(12) United States Patent
O'Donnell et al.

(10) Patent No.: US 8,911,397 B2
(45) Date of Patent: Dec. 16, 2014

(54) STEERABLE SHEATH HANDLE PULLEY MECHANISM

(71) Applicants: Joseph A. O'Donnell, Escondido, CA (US); Steven T. Onishi, Cupertino, CA (US)

(72) Inventors: Joseph A. O'Donnell, Escondido, CA (US); Steven T. Onishi, Cupertino, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 13/722,589

(22) Filed: Dec. 20, 2012

(65) Prior Publication Data

US 2013/0184642 A1     Jul. 18, 2013

Related U.S. Application Data

(60) Provisional application No. 61/579,097, filed on Dec. 22, 2011.

(51) Int. Cl.
| | |
|---|---|
| *A61M 25/00* | (2006.01) |
| *A61M 25/01* | (2006.01) |
| *A61M 39/10* | (2006.01) |
| *A61B 1/00* | (2006.01) |
| *A61M 39/06* | (2006.01) |
| *A61B 1/015* | (2006.01) |

(52) U.S. Cl.
CPC ....... *A61M 25/0147* (2013.01); *A61M 25/0097* (2013.01); *A61M 25/0136* (2013.01); *A61M 39/1055* (2013.01); *A61B 1/00066* (2013.01); *A61M 39/06* (2013.01); *A61B 1/015* (2013.01)
USPC ....................................... 604/95.04; 600/585

(58) Field of Classification Search
CPC ..................... A61M 25/0147; A61M 25/0136; A61B 2017/003
USPC ................................ 604/95.04, 528; 600/585
See application file for complete search history.

(56) References Cited

U.S. PATENT DOCUMENTS 5,370,624 A    12/1994    Edwards et al.
6,245,045 B1    6/2001    Stratienko
(Continued)

FOREIGN PATENT DOCUMENTS

EP    0566426 A1    10/1993
EP    1050316 B1    12/2003
(Continued)

OTHER PUBLICATIONS

International Search Report and Written Opinion issued in PCT/US2012/071058, mailed Feb. 28, 2013, 16 pages.

(Continued)

*Primary Examiner* — Theodore Stigell
*Assistant Examiner* — Benjamin Koo
(74) *Attorney, Agent, or Firm* — Faegre Baker Daniels LLP

(57) ABSTRACT

Various embodiments concern an introducer sheath assembly comprising a tubular sheath member having a deflectable distal end portion and a sheath member lumen, and a handle assembly including a steering mechanism for deflecting the distal end portion of the sheath member. The distal end portion of the sheath member can deflect in different directions along a plane by selective tension in one of two pull wires. The selective tension can be caused by selective proximal or distal axial translation of a shuttle assembly relative to the tubular sheath member. The selective proximal or distal axial translation can be controlled by selective clockwise or counterclockwise rotation of a control knob.

19 Claims, 7 Drawing Sheets

(56) References Cited

U.S. PATENT DOCUMENTS

| | | | |
|---|---|---|---|
| 2005/0277874 A1* | 12/2005 | Selkee | 604/95.04 |
| 2006/0142699 A1 | 6/2006 | Lampropoulos | |
| 2008/0039918 A1* | 2/2008 | Falwell et al. | 607/122 |
| 2009/0281524 A1* | 11/2009 | Scheibe et al. | 604/528 |
| 2013/0165857 A1 | 6/2013 | O'Donnell et al. | |

FOREIGN PATENT DOCUMENTS

| | | | |
|---|---|---|---|
| EP | 1607118 | B1 | 12/2005 |
| EP | 2116272 | B1 | 11/2009 |
| EP | 2204208 | A2 | 7/2010 |
| EP | 2438954 | A1 | 4/2012 |
| EP | 2465568 | A1 | 6/2012 |
| WO | WO9841275 | A1 | 9/1998 |
| WO | WO2012114633 | A1 | 8/2012 |

OTHER PUBLICATIONS

International Search Report and Written Opinion issued in PCT/US2012/071084, mailed Mar. 8, 2013, 19 pages.

\* cited by examiner

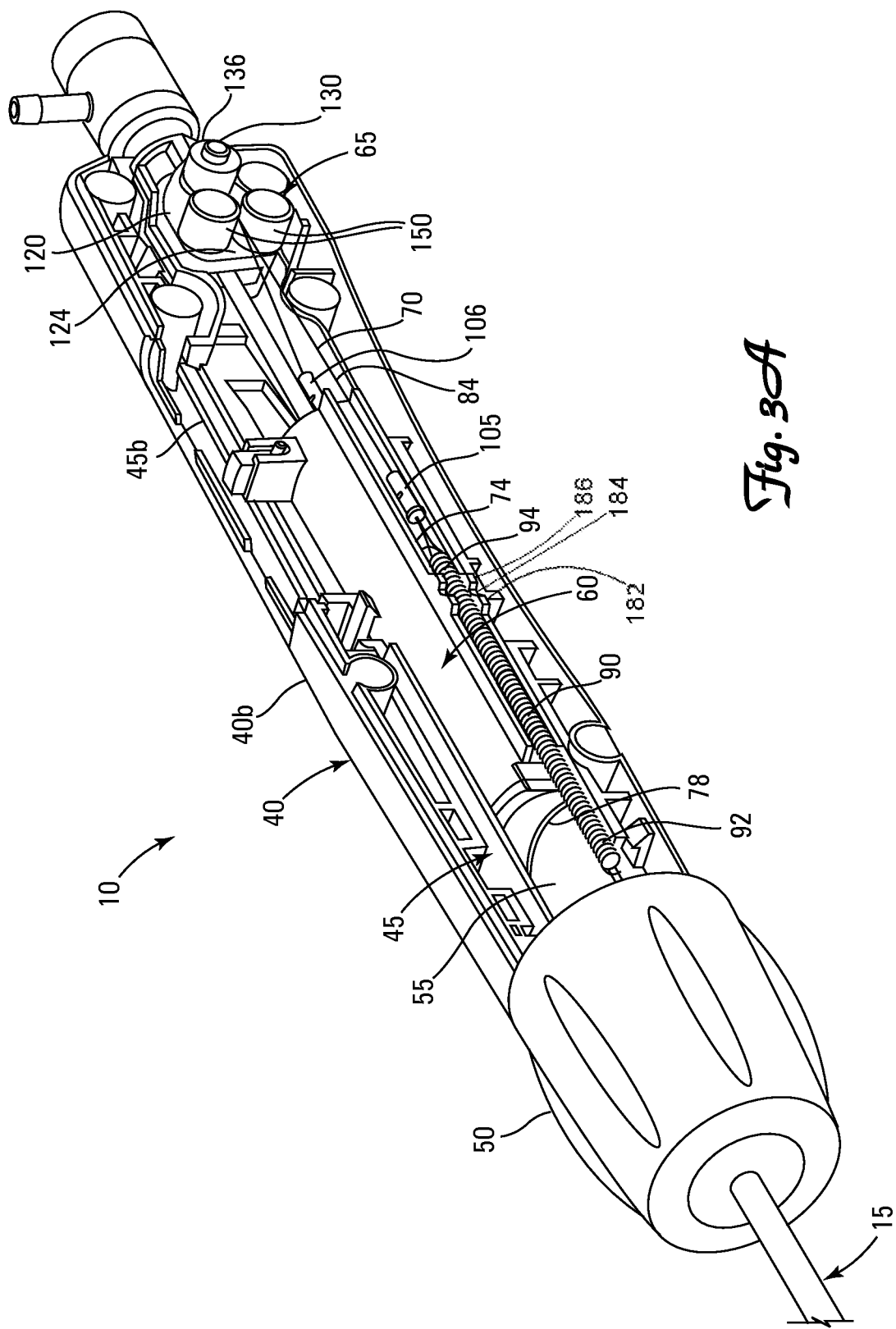

STEERABLE SHEATH HANDLE PULLEY MECHANISM

CROSS-REFERENCE TO RELATED APPLICATION

This application claims priority to U.S. Provisional Application No. 61/579,097, filed Dec. 22, 2011, which is herein incorporated by reference in its entirety.

TECHNICAL FIELD

The present invention relates to medical introducer sheaths for introducing medical devices into the body. In particular, the present invention relates to deflectable introducer sheaths.

BACKGROUND

Introducer sheaths are important instruments for use in medical diagnostic and therapeutic procedures. In particular, introducer sheaths can be used by a clinician to access target areas of the patient's anatomy, e.g., the patient's cardiovascular system, and also allow for diagnostic and/or therapeutic payloads (such as ablation catheters) to be inserted into these target areas. Certain types of known introducer sheaths are so-called "deflectable" or "steerable" introducer sheaths, which include mechanisms for altering the shape of the sheath to facilitate navigation of the patient anatomy.

SUMMARY

Example 1 concerns a deflectable introducer sheath assembly comprising: a tubular sheath member having a proximal end portion including a proximal end, a distal end portion terminating in a distal tip, and an internal sheath lumen extending through the proximal and distal end portions of the sheath member; and a handle assembly coupled to the proximal end portion of the sheath member. The handle assembly can include an outer housing, a control knob axially rotatable relative to the outer housing, a drive shaft within the outer housing and rotatable with the control knob relative to the outer housing, a shuttle assembly disposed about and operably engaged with the drive shaft such that rotation of the control knob and drive shaft relative to the outer housing causes axial translation of the shuttle assembly relative to the drive shaft within the outer housing, an inner housing within the outer housing enclosing the shuttle assembly, and a pulley assembly located proximal to the drive shaft and the shuttle assembly within the inner housing. The pulley assembly can include: a pulley support member having a first side and an opposite second side; a first pulley shaft extending laterally from the first side of the pulley support member; a first pulley wheel mounted on the first pulley shaft; a second pulley shaft extending laterally from the second side of the pulley support member; and a second pulley wheel mounted on the second pulley shaft. The deflectable introducer sheath assembly can further include a first pull wire having a distal end portion connected to the sheath member proximate the distal tip thereof, and a proximal end portion extending into the handle assembly, the proximal end portion of the first pull wire extending around and supported by the first pulley wheel and operably coupled to the shuttle assembly; and a second pull wire having a distal end portion connected to the sheath member proximate the distal tip thereof, and a proximal end portion extending into the handle assembly, the proximal end portion of the second pull wire extending around and supported by the second pulley wheel and operably coupled to the shuttle assembly. Axial rotation of the control knob in a first direction of rotation causes the shuttle assembly to translate proximally relative to the sheath member and thereby apply tension to the distal end portion of the first pull wire to deflect the distal end portion of the sheath member in a first direction of deflection. Further, axial rotation of the control knob in a second direction of rotation opposite the first direction of rotation causes the shuttle assembly to translate distally relative to the sheath member and thereby apply tension to the distal end portion of the second pull wire to deflect the distal end portion of the sheath member in a second direction of deflection to provide bi-directional deflectability in the sheath member.

In example 2, the introducer sheath assembly of example 1, wherein the handle assembly further comprises a first spring having a first end connected to the inner housing or the outer housing and a second end connected to the first pull wire, and a second spring having a third end connected to the inner housing or the outer housing and a fourth end connected to the second pull wire, the first and second springs operable at least in part to eliminate slack in the first pull wire and the second pull wire, respectively, as the shuttle assembly translates relative to the sheath member.

In example 3, the introducer sheath assembly of either of examples 1 or 2, wherein the handle assembly further includes a first stop member fixedly connected to the first pull wire and configured to engage the shuttle assembly, and a second stop member fixedly connected to the second pull wire and configured to engage the shuttle assembly.

In example 4, the introducer sheath assembly of example 3, wherein: engagement between the shuttle assembly and the first stop member during proximal translation of the shuttle assembly relative to the sheath member increases tension within the first pull wire to deflect the distal end portion, and engagement between the shuttle assembly and the second stop member during distal translation of the shuttle assembly relative to the sheath member increases tension within the second pull wire to deflect the distal end portion.

In example 5, the introducer sheath assembly of example 4, wherein the shuttle assembly can only engage with one of the first stop member and the second stop member a time.

In example 6, the introducer sheath assembly of example 3, wherein the first stop member is a first crimp tube crimped over the first wire and the second stop member is a second crimp tube crimped over the second wire.

In example 7, the introducer sheath assembly of any preceding example, wherein: axial rotation of the control knob in the first direction of rotation causes the distal end portion to assume a first shape having a first curvature, axial rotation of the control knob in the second direction of rotation causes the distal end portion to assume a second shape having a second curvature, and the first shape is different than the second shape and the first curvature is different than the second curvature.

In example 8, the introducer sheath assembly of any preceding example, wherein the first direction of deflection of the distal end portion is along the same plane as the second direction of deflection of the distal end portion.

In example 9, the introducer sheath assembly of any preceding example, further comprising a feedback mechanism comprising a first detent feature on the shuttle assembly and a second detent feature on the inner handle assembly, wherein engagement between the first detent feature and the second detent feature generates feedback indicating a neutral state of the introducer sheath assembly to a user, wherein the feedback comprises at least one of sound and tactile feedback.

Example 10 concerns a deflectable introducer sheath assembly comprising: a tubular sheath member having a proximal end portion including a proximal end, a distal end portion terminating in a distal tip, and an internal sheath lumen extending through the proximal and distal end portions of the sheath member; and a handle assembly coupled to the proximal end portion of the sheath member. The handle assembly can comprise: a housing; a control knob axially rotatable relative to the housing; a drive shaft within the housing and fixed relative to the control knob to be rotatable by the control knob; a shuttle assembly disposed about and operably engaged with the drive shaft such that rotation of the drive shaft causes axial translation of the shuttle assembly relative to the housing; and a pulley assembly located proximal to the drive shaft and the shuttle assembly within the inner housing. The deflectable introducer sheath assembly can further include a first pull wire having a distal end portion connected to the sheath member proximate the distal tip thereof, and a proximal end portion extending into the handle assembly, the proximal end portion of the first pull wire supported by the pulley assembly; and a second pull wire having a distal end portion connected to the sheath member proximate the distal tip thereof, and a proximal end portion extending into the handle assembly, the proximal end portion of the second pull wire supported by the pulley assembly. Rotation of the control knob in a first direction of rotation causes the shuttle assembly to translate proximally relative to the sheath member and thereby apply tension to the distal end portion of the first pull wire to deflect the distal end portion of the sheath member in a first direction of deflection, and wherein axial rotation of the control knob in a second direction of rotation opposite the first direction of rotation causes the shuttle assembly to translate distally relative to the sheath member and thereby apply tension to the distal end portion of the second pull wire to deflect the distal end portion of the sheath member in a second direction of deflection.

In example 11, the introducer sheath assembly of example 10, wherein the handle assembly further comprises a first spring having a first end connected to the housing and a second end connected to the first pull wire, and a second spring having a third end connected to the housing and a fourth end connected to the second pull wire, the first and second springs operable at least in part to eliminate slack in the first pull wire and the second pull wire, respectively, as the shuttle assembly translates relative to the sheath member.

In example 12, the introducer sheath assembly of either of examples 10 and 11, wherein the handle assembly further includes a first stop member fixedly connected to the first pull wire and configured to engage the shuttle assembly, and a second stop member fixedly connected to the second pull wire and configured to engage the shuttle assembly.

In example 13, the introducer sheath assembly of example 12, wherein: engagement between the shuttle assembly and the first stop member during proximal translation of the shuttle assembly relative to the sheath member increases tension within the first pull wire to deflect the distal end portion, and engagement between the shuttle assembly and the second stop member during distal translation of the shuttle assembly relative to the sheath member increases tension within the second pull wire to deflect the distal end portion.

In example 14, the introducer sheath assembly of example 13, wherein the shuttle assembly can only engage with one of the first stop member and the second stop member a time.

In example 15, the introducer sheath assembly of example 12, wherein the first stop member is a first crimp tube crimped over the first wire and the second stop member is a second crimp tube crimped over the second wire.

In example 16, the introducer sheath assembly of any of examples 10-15, wherein: axial rotation of the control knob in the first direction of rotation causes the distal end portion to assume a first shape having a first curvature, axial rotation of the control knob in the second direction of rotation causes the distal end portion to assume a second shape having a second curvature, and the first shape is different than the second shape and the first curvature is different than the second curvature.

In example 17, the introducer sheath assembly of any of examples 10-16, further comprising a feedback mechanism comprising a first detent feature and a second detent feature, the first detent feature connected to the shuttle assembly such that the first detent feature translates axially relative to the second detent feature when the control knob is axially rotated relative to the tubular sheath, wherein engagement between the first detent feature and the second detent feature generates feedback indicating a neutral state of the introducer sheath assembly to a user, wherein the feedback comprises at least one of sound and tactile feedback.

In example 18, the introducer sheath assembly of example 17, wherein the neutral state corresponds with a state of neutral tension within the first pull wire and the second pull wire.

Example 19 concerns a deflectable introducer sheath assembly comprising: a tubular sheath member having a proximal end portion including a proximal end, a distal end portion terminating in a distal tip, and an internal sheath lumen extending through the proximal and distal end portions of the sheath member; and a handle assembly coupled to the proximal end portion of the sheath member. The handle assembly can comprise: a housing; a control knob axially rotatable relative to the tubular sheath; a drive shaft within the housing and rotatable by the control knob; a shuttle assembly operably engaged with the drive shaft such that rotation of the drive shaft causes axial translation of the shuttle assembly relative to the tubular sheath; a first pull wire connected to the sheath member to deflect the distal end portion of the sheath member; a second pull wire connected to the sheath member to deflect the distal end portion of the sheath member; and a pulley assembly distal of the drive shaft and the shuttle assembly, the pulley assembly supporting one or both of the first pull wire and the second pull wire. Rotation of the control knob in a first direction of rotation can cause the shuttle assembly to translate proximally relative to the sheath member and engage a first stop feature to apply tension in the first pull wire. Axial rotation of the control knob in a second direction of rotation opposite the first direction of rotation can cause the shuttle assembly to translate distally relative to the sheath member and engage a second stop feature to apply tension in the second pull wire.

In example 20, the introducer sheath assembly of example 19, further comprising a feedback mechanism comprising a first detent feature and a second detent feature, the first detent feature connected to the shuttle assembly such that the first detent feature translates axially relative to the second detent feature when the control knob is axially rotated relative to the tubular sheath, wherein engagement between the first detent feature and the second detent feature generates feedback indicating a neutral state of the introducer sheath assembly to a user.

While multiple embodiments are disclosed, still other embodiments of the present invention will become apparent to those skilled in the art from the following detailed description, which shows and describes illustrative embodiments of

BRIEF DESCRIPTION OF THE DRAWINGS

FIGS. 3A and 3B are isometric views of the left and right sides, respectively, of the proximal portion of the introducer sheath assembly of FIG. 1A each with portions of the handle assembly removed.

Figure 1A:
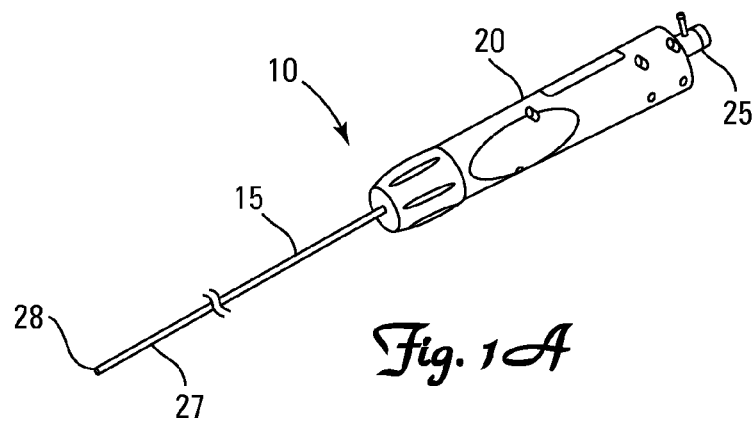
FIG. 1A is an isometric view of an exemplary introducer sheath assembly according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1A is a plan view of an exemplary introducer sheath assembly 10 according to one embodiment of the present invention. The introducer sheath assembly 10 is configured for use in a broad range of medical procedures requiring the introduction of a payload into the body. For example, in various embodiments, the introducer sheath assembly 10 can be used to introduce therapeutic and/or diagnostic electrophysiology catheters, e.g., ablation and/or mapping catheters, into a heart chamber. In other embodiments, the introducer sheath assembly 10 can be used to deliver implantable devices, e.g., pacing leads, to a heart chamber or to a coronary vein. In short, the present invention is not limited to any particular clinical use.

As shown in FIG. 1A, the introducer sheath assembly 10 includes a sheath member 15, a handle assembly 20 and a hemostasis valve assembly 25. In the illustrated embodiment, the handle assembly 20 is coupled to the sheath member 15 distal to the hemostasis valve assembly 25, which occupies the proximal-most position on the introducer sheath assembly 10. As will be explained in further detail below, the sheath member 15 includes a lumen extending longitudinally therethrough sized to allow introduction of a payload into the introducer sheath assembly 10 and out the distal end of the sheath member 15. Additionally, in various embodiments, the sheath member 15 includes a deflectable distal end portion 27 that can assume a variety of different shapes for navigating the patient anatomy, and as shown in FIG. 1A, terminates in a distal tip 28.

Figure 1B:
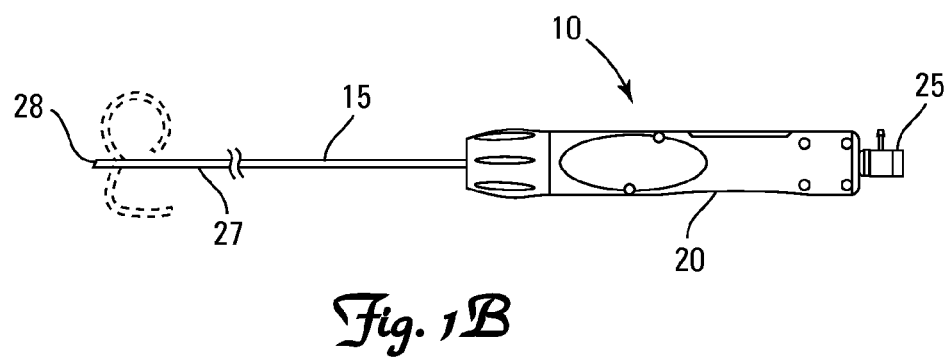
FIG. 1B is a plan view of the introducer sheath assembly of FIG. 1A illustrating the deflectability of the sheath according to one embodiment of the present invention.

In general, the handle assembly 20 is configured to allow a clinician to manipulate and control the introducer sheath assembly 10, and in particular, includes a mechanism for altering the shape of the distal end portion 27 of the sheath member 15 to assist in navigating the patient anatomy, as explained in further detail below. Finally, the hemostasis valve assembly 25 is configured to allow introduction of a payload into the lumen of the sheath member 15 while at the same time inhibiting unintended leakage of fluid from the sheath member 15 into the operating environment and/or aspiration of air into the sheath member 15 lumen. In the various embodiments illustrated, the introducer sheath assembly 10 is a deflectable or steerable introducer sheath, in that the shape or profile of at least the distal end portion 27 of the sheath member 15 can be altered, i.e., by manipulation of a steering mechanism in the handle assembly 20, to facilitate navigation of the patient anatomy. FIG. 1B is a plan view of the introducer sheath assembly 10 illustrating the deflectability of the sheath member 15 according to one embodiment of the present invention. As indicated by the phantom lines in FIG. 1B, the distal end portion 27 can be deflected relative to its "straight" or undeflected state shown in FIG. 1A. As further shown, in various embodiments, the introducer sheath assembly 10 is a "bi-directional" steerable sheath, in that the deflection of the distal end portion 27 can occur in two "directions" relative to the longitudinal axis of the introducer sheath assembly 10 depending on the manner in which the clinician manipulates the steering mechanism in the handle assembly 20, as will be explained in further detail below.

Additionally, in the embodiment shown in FIG. 1B, the introducer sheath assembly 10 is asymmetrically deflectable, in that the distal end portion 27 of the sheath member 15 can assume different profiles or shapes when fully deflected in different directions relative to the longitudinal axis of the introducer sheath assembly 10. For example, as indicated by the upper phantom lines in FIG. 1B, when fully deflected in one direction, the distal end portion 27 of the sheath member 15 curls into substantially a 360 degree arc. In contrast, as indicated by the lower phantom lines in FIG. 1B, when fully deflected in an opposite direction the distal end portion 27 generally assumes a J-shape defined by an arc of approximately 180 degrees followed by a distal segment that is oriented substantially parallel to the undeflected portion of the sheath member 15.

As will be explained in greater detail elsewhere, deflection of the distal end portion 27 of the sheath member 15 is effectuated by the inclusion of pull wires (not shown in FIGS. 1A and 1B) extending within the sheath member 15 and fixedly connected to the sheath member 15 within the distal end portion 27 at one end, and to the handle assembly 20 at the other end. In various embodiments, these pull wires are each secured to the sheath member 15 near its distal tip 28 (e.g., by attaching the pull wires to an anchor member incorporated into the sheath member 15) such that the distal ends of the pull wires are fixed relative to the sheath member 15. Accordingly, by selectively applying tension to the respective pull wires (e.g., via the steering mechanism, described in greater detail below, incorporated into the handle assembly 20), the distal end portion 27 is deflected as indicated by the phantom lines in FIG. 1B. Except as specifically discussed herein, however, the specific configuration of the pull wires, including the means for attaching the pull wires to the distal end portion 27 of the sheath member 15, and the means by which the pull wires are incorporated into the sheath member 15, is not of particular importance to the various embodiments of the present invention. Thus, the embodiments of the present invention are not in any way limited by the technique by which the pull wires are routed through the sheath member 15 or secured to the distal end portion 27 thereof.

In addition, except as otherwise discussed herein, the particular construction of the sheath member 15 in the various embodiments is not critical, and thus will not be discussed in great detail. In short, any number of construction details can be utilized for the sheath member 15 within the scope of the embodiments of the present invention. For example, the sheath member can have a single or multiple layer polymer construction, and may or may not include one or more reinforcing elements (e.g., braids, coils, wires, etc.) to enhance the mechanical characteristics, e.g., stiffness, torquability and the like, of the sheath member 15. In one embodiment, the sheath member 15 includes an outer layer of a biocompatible polymer such as a polyether block amide, an inner layer of a lubricious polymeric material such as polytetrafluoroethylene (PTFE), ethylene tetrafluoroethylene (ETFE), silicone, and the like, with a stainless steel braid and/or stainless steel wire coil embedded between the outer and inner polymer layers. In various embodiments, the durometer of the polymeric materials making up the outer and/or inner layers may be varied along the length of the sheath member 15 to further tailor the mechanical characteristics to the needs of the end user. Again, unless specifically discussed herein, the construction of the sheath member 15 is in no way limited to any particular construction.

Figure 2:
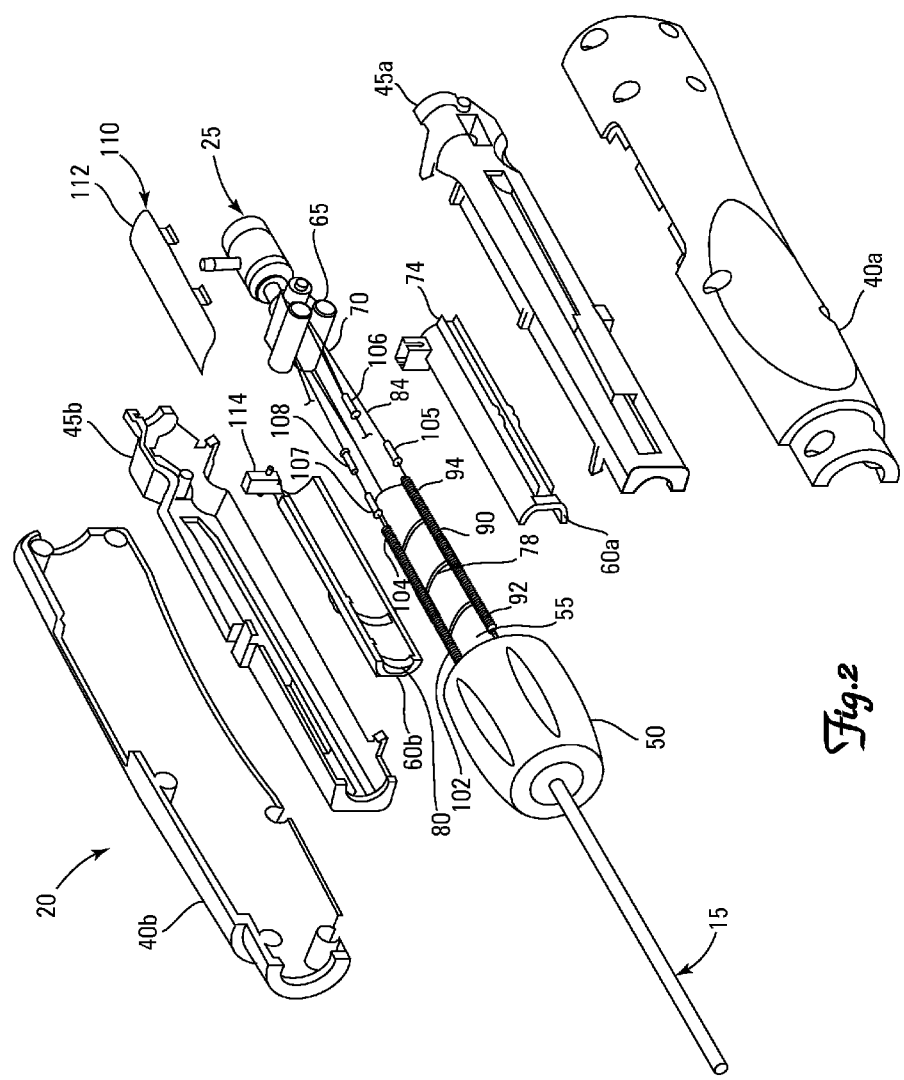
FIG. 2 is an isometric view of the proximal portion of the introducer sheath assembly of FIG. 1A showing its handle assembly in an exploded view.

FIG. 2 is an isometric view of the proximal portion of the introducer sheath assembly 10 showing the handle assembly 20 in an exploded view. As shown in FIG. 2, the handle assembly 20 includes an outer housing assembly 40 comprised of left and right outer housing portions 40a, 40b, an inner housing assembly 45 comprised of left and right inner housing portions 45a, 45b, a control knob 50, a drive shaft 55, a shuttle assembly 60 comprised of left and right shuttle portions 60a, 60b, and a pulley assembly 65. As further shown, the introducer sheath assembly 10 includes a left-side pull wire 70 and a right-side pull wire 75. The drive shaft 55 is fixed to, or in some embodiments, integrally formed with, the control knob 50, and both are axially rotatable relative to the sheath member 15 and the housing assemblies 40, 45 and the shuttle assembly 60. When assembled, the shuttle portions 60a, 60b join together and are positioned about the drive shaft 55, the inner housing assembly portions 45a, 45b are joined together and are positioned around the shuttle assembly 60, and the outer housing portions 40a, 40b are joined together and are positioned about the inner housing assembly 45, thus forming an outer enclosure for the handle assembly 20. In the illustrated embodiment, the outer housing portions 40a, 40b, the inner housing portions 45a, 45b and the shuttle portions 60a, 60b include features, e.g., fastener sockets, snap-fit features, etc., to facilitate joining the respective parts together. It will be appreciated that the specific techniques for joining these elements are not critical to the various embodiments of the invention, and thus are not discussed in detail herein.

The drive shaft 55 includes external threads 78, and the shuttle assembly 60 includes mating internal threads 80 (visible on the shuttle portion 60b in FIG. 2). The drive shaft 55 is axially rotatable relative to the shuttle assembly 60 (as well as, among other elements, the inner housing assembly 45, the outer housing assembly 40 and, as discussed previously, the sheath member 15). For example, the drive shaft 55 can be axially rotated by rotating the control knob 50 while holding the handle assembly 20 by the outer housing assembly 40. The shuttle assembly 60 can translate axially relative to the inner housing assembly 45 and the outer housing assembly 40. Accordingly, the external rails 74 (visible on shuttle portion 60a in FIG. 2) that mate with the inner housing portions 45a, 45b, can translate axially relative to the inner housing portions 45a, 45b in a manner allowing the shuttle assembly 60 to slide axially within the inner housing 45. At the same time, the shuttle assembly 60 is rotationally fixed relative to the housing assemblies 40, 45.

The mating threads 78, 80 operate to operably engage the shuttle assembly 60 with the drive shaft 55 such that rotation of the control knob 50 and the drive shaft 55 relative to shuttle assembly 60 (as well as the outer housing assembly 40 and the inner housing assembly 45) causes axial translation of the shuttle assembly relative to the drive shaft 55 within the outer housing assembly 40 and the inner housing assembly 45. In the illustrated embodiment, rotation of the control knob 50 and the drive shaft 55 in one rotational direction will cause the shuttle assembly 60 to translate axially in the distal direction, while rotation of the control knob 50 and the drive shaft 55 in the opposite rotational direction will cause the shuttle assembly 60 to translate axially in the proximal direction. The orientation of the threads 78, 80 determines the direction of axial translation of the shuttle assembly 60 in response to rotation of the control knob 50 and the drive shaft 55.

As will be explained in further detail below, the left side pull wire 70 includes a proximal end portion 84 that extends within the handle assembly 20 and is operably coupled to the shuttle assembly 60. In addition, the right side pull wire 75 includes a proximal end portion 88 that extends within the handle assembly 20 and is also operably coupled to the shuttle assembly 60. As explained previously, each of the pull wires 70, 75 has a distal end portion (not shown) fixedly connected to the sheath member 15 in the distal end portion 27 thereof. As such, the pull wires 70, 75 are operably coupled to the shuttle assembly 60 such that upon sufficient axial translation of the shuttle assembly 60, either the pull wire 70 or the pull wire 75 will be placed under tension (depending on the direction of translation of the shuttle assembly 60), causing deflection of the distal end portion 27 of the sheath member 15 as shown in FIG. 1B. The pulley assembly 65 operates to support and guide the pull wires 70, 75 during operation of the introducer sheath assembly 10 and deflection of the distal end portion 27 of the sheath member 15.

As can be further seen in FIG. 2, the handle assembly 20 further includes a left side spring 90 having opposite ends 92, 94, and a right side spring 98 having opposite ends 102, 104. In various embodiments, the end 92 of the spring 90 is connected, either directly or indirectly, to the inner housing 45 or the outer housing 40, while the end 94 is connected to the 70 pull wire. In addition, the end 102 of the spring 98 is connected, either directly or indirectly, to the inner housing 45 or the inner housing 40, while the end 104 is connected to the pull wire 75. The springs 90, 98 operate at least in part, to maintain a desired amount of tension in the respective pull wires 70, 75 during operation of the deflection mechanism of the handle assembly 20. Thus, for example, the springs 90, 98 are operable at least in part to eliminate slack in the pull wires 70, 75, respectively, as the shuttle assembly 60 translates axially to cause deflection of the sheath member 15. As further shown, crimp tubes 105, 106 are attached to the pull wire 70, while crimp tubes 107, 108 are attached to the pull wire 75. The crimp tube 105 operates to secure the pull wire 70 to the end 94 of the spring 90, while the crimp tube 106 operates as a stop member to engage the shuttle assembly 60 and thereby couples the pull wire 70 to the shuttle assembly 60 during operation of the introducer sheath assembly 10 deflection mechanism. Similarly, the crimp tube 107 operates to secure the pull wire 75 to the end 104 of the spring 98, and the crimp tube 108 operates to engage the shuttle assembly 60 and thereby couples the pull wire 75 to the shuttle assembly 60. It is emphasized, however, that while the illustrated embodiment utilized crimp tubes, any number of suitable coupling structures and/or coupling techniques can be utilized to perform the foregoing functions.

As further shown in FIG. 2, the handle assembly 20 includes a deflection indicator assembly 110 including a window 112 and an indicator tab 114 coupled to the shuttle assembly 60 which, when assembled, provides a visual indication of, for example, the degree of deflection of the distal end portion of the sheath member 15. In various embodiments, other visual indicators can be employed, or such indicators may be omitted altogether.

Figure 3B:
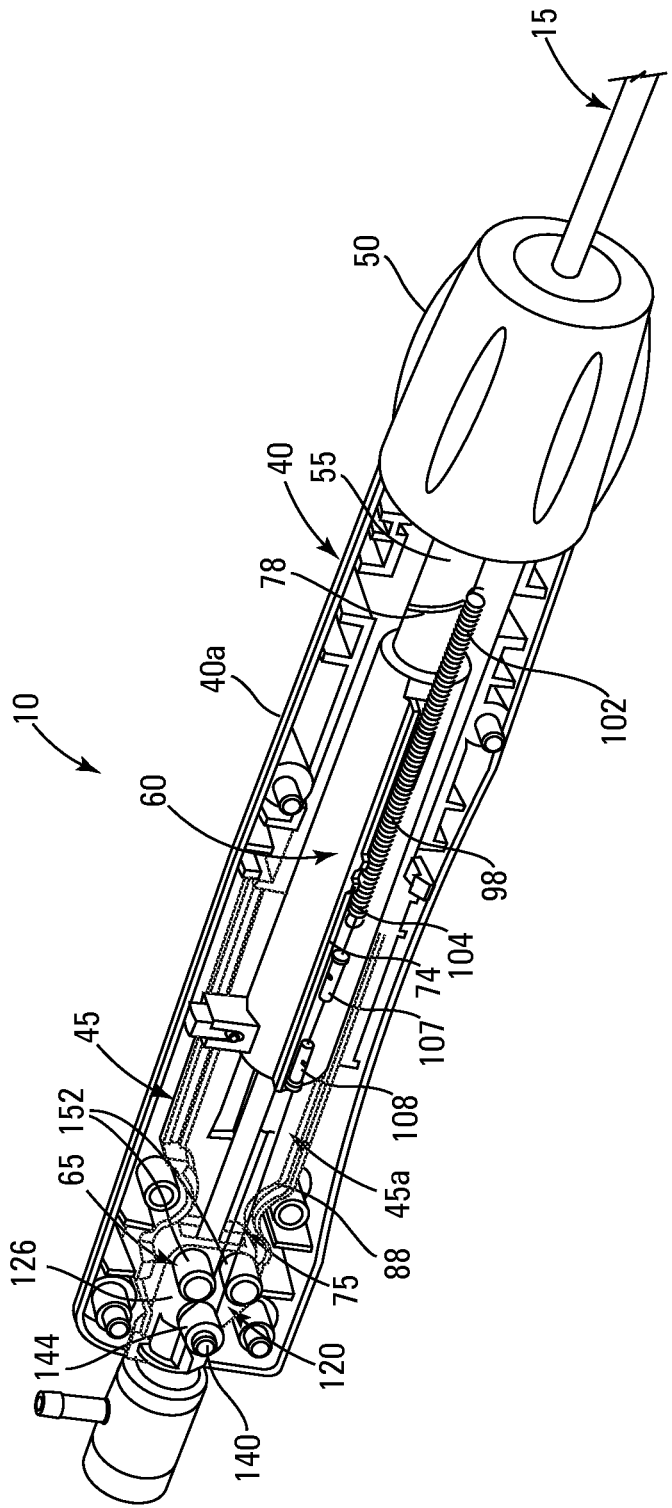
Figure 4A:
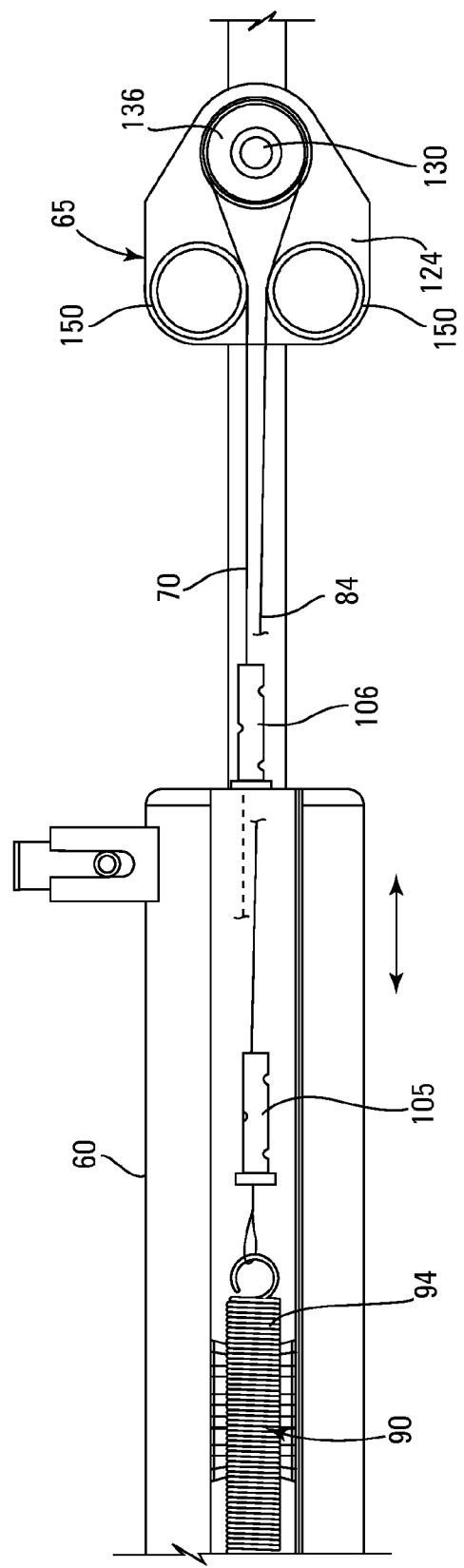
FIGS. 4A and 4B are left and right elevation views of a portion of the handle assembly of the introducer sheath assembly of FIG. 1A illustrating the configuration for connecting the pull wires to the handle assembly according to one embodiment of the present invention.
Figure 4B:
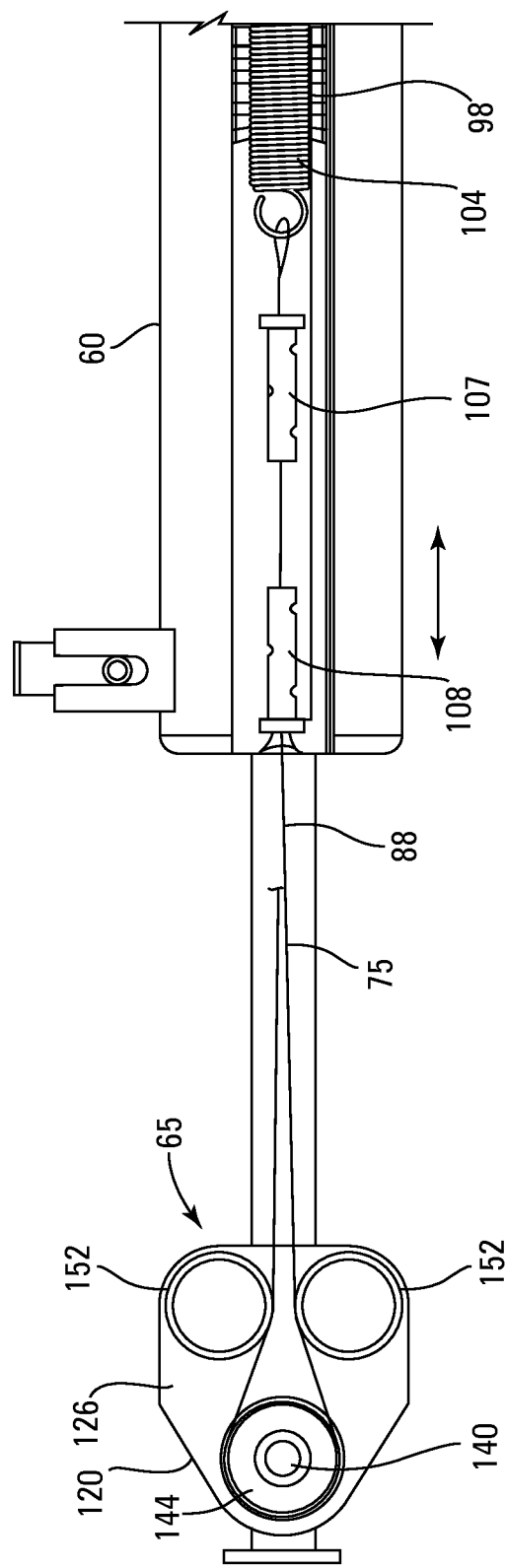

To further illustrate the construction and functionality of the handle assembly 20 and the pull wires 70, 75, reference is made to FIGS. 3A-3B and 4A-4B. FIGS. 3A and 3B are isometric views of the left and right sides, respectively, of the proximal portion of the introducer sheath assembly 10 each with the outer housing portions 40a, 40b and the inner housing portions 45a, 45b, respectively, removed. FIGS. 4A and 4B are left and right elevation views of a portion of the introducer sheath assembly 10 illustrating the pulley assembly 65 and the configuration by which the pull wires 70, 75 are coupled to the shuttle assembly 60. As shown, the pulley assembly 65 includes a pulley support member 120 having a left side 124 and a right side 126, a left pulley shaft 130 extending laterally from the left side 124, a left pulley wheel 136 mounted on the left pulley shaft 130, a right pulley shaft 140 extending laterally from the right side 126 of the pulley support member 120, and a right pulley wheel 144 mounted on the right pulley shaft 140. As further shown, extending laterally from each side 124, 126 of the pulley support member 120 are a plurality of wire guide members 150, 152, respectively.

As illustrated, the proximal portion 84 of the left pull wire 70 is coupled to the end 94 of the spring 90, extends around and is supported by the left pulley wheel 136, and is operably coupled to the left shuttle portion 60a by means of the crimp tube 106 abutting the end of the left shuttle portion 60a. The left pull wire 70 further extends through the crimp tube 106 and is routed into the shaft of the sheath member 15 to the distal end portion 27 thereof, as explained above. As further shown, the guide members 150 operate to support and guide the left pull wire 70 as it extends around the pulley wheel 136. The crimp tube 106 is selectively positioned and secured to the pull wire 70 so as to permit a desired amount of translation of the shuttle assembly 60 in the proximal direction before the crimp tube 106 will engage the left shuttle portion 60a. Once the shuttle assembly 60 contacts the crimp tube 106, as shown, further proximal translation of the shuttle assembly 60 causes the pull wire 70 to be placed in tension (i.e., because it is secured to the distal end portion 27 of the sheath member 15) to cause deflection of the distal end portion 27 of the sheath member 15. As will be apparent, translation of the shuttle assembly 60 in the distal direction will tend to release this tension in the pull wire 70, to the point at which the crimp tube 106 no longer abuts the shuttle portion 60a. However, as discussed above, the spring 90 will continue to maintain a desired amount of tension in the pull wire 70 to inhibit formation of undesired slack.

As further shown, the proximal portion 88 of the right pull wire 75 is coupled to the end 104 of the spring 98, extends around and is supported by the right pulley wheel 144, and is operably coupled to the right shuttle portion 60b by means of the crimp tube 108 abutting the end of the right shuttle portion 60a. The right pull wire 75 further extends through the crimp tube 107 and is routed into the shaft of the sheath member 15 to the distal end portion 27 thereof, as explained above. As further shown, the guide members 152 operate to support and guide the right pull wire 75 as it extends around the pulley wheel 144. The crimp tube 107 engages the right shuttle portion 60b, such that distal translation of the shuttle assembly 60 causes the pull wire 75 to be placed in tension (i.e., because it is secured to the distal end portion 27 of the sheath member 15) to cause deflection of the distal end portion 27 of the sheath member 15. As will be apparent, translation of the shuttle assembly 60 in the proximal direction will tend to release this tension in the pull wire 75. However, as discussed above, the spring 98 will continue to maintain a desired amount of tension in the pull wire 75 to inhibit formation of undesired slack.

The handle assembly 20 provides an elegant means for deflecting and steering the distal end portion 27 of the sheath member 15, providing good tactile feedback to the clinician as well as optimal control of the degree of deflection.

Various embodiments can include a feedback mechanism that provides feedback to indicate a neutral state. The neutral state may correspond to a state of neutral tension within the left and right pull wires 70, 75. As discussed above, the shuttle assembly 60 moves axially relative to the inner housing assembly 45 due to rotation of the drive shaft 55, the drive shaft 55 rotated by rotation of the control knob 50 by a user. The inner housing assembly 45 can have a first detent feature that moves along the shuttle assembly 60 (e.g., along the external rails 74) during relative axial movement between the shuttle assembly 60 and the inner housing assembly 45. The first detent feature may be located approximately in the longitudinal center of the inner housing assembly 45A. The shuttle assembly 60A can further include a second detent feature along the longitudinal pathway that the first detent feature moves along during relative axial movement. The first detent feature can be complementary to the second detent feature such that engagement of the first detent feature with the second detent feature generates feedback. The feedback can be a noise (e.g., a "click" sound), tactile feedback felt by the user handling the handle assembly (e.g., the feeling of a detent snapping into place), and/or changes in the resistance to movement felt from rotation of the control knob 50 (e.g., temporarily increasing or decreasing the resistance to rotation of the control knob 50 relative to the outer housing assembly 40).

Figure 5:
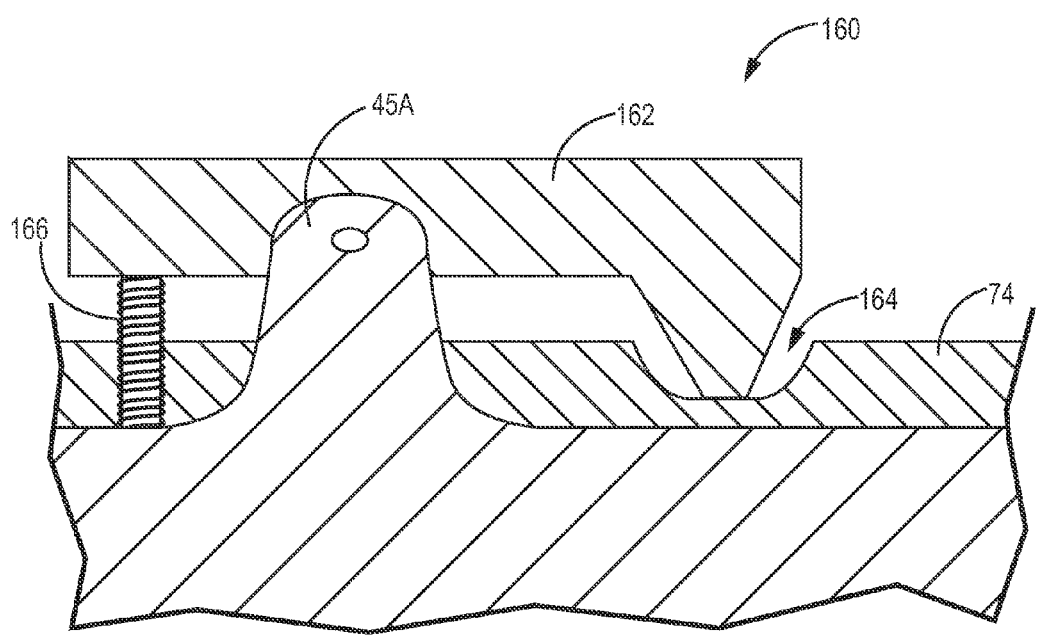
FIG. 5 is an isometric view of a feedback mechanism of the handle assembly according to one embodiment of the present invention.

FIG. 5 illustrates an isometric view of a feedback mechanism 160. The feedback mechanism 160 can comprise a first detent feature 162 attached to the inner housing assembly 45A. As show in FIG. 5, the first detent feature 162 is a tab. The tab is biased by the spring 166 and rotatably attached to the inner housing assembly 45 to force the first detent feature 162 against the external rails 74 of the shuttle assembly 60. The shuttle assembly 60 includes a second detent feature 164. As shown in FIG. 5, the second detent feature 164 is a trough in the external rails 74 of the shuttle assembly 60. The tab of the first detent feature 162 can run along the external rails 74 as the shuttle assembly 60 translates axially relative to the inner housing assembly 45. Feedback (e.g., sound, tactile event, change in resistance) can be produced when the tab of the first detent feature 162 is forced into the trough of the second detent feature 164. Increased force may be needed to be input by the user to drive the tab out of the trough. In some cases, a distal ramp and/or an axial ramp is provided along the rails 74 leading up to the trough such that an increase in resistance is felt by the user before the tab is forced into the trough. FIG. 3A shows a proximal ramp 186 and a distal ramp 186 with a trough 184 therebetween, along the rails 74 of the shuttle assembly 60. While the first detent feature 162 corresponds to a biased tab and the second detent feature 164 corresponds to a trough in FIG. 5, various other embodiments are not so limited. For example, the first detent feature 162 could instead be a trough and the second detent feature 164 could correspond to the biased tab. Other options for the first detent feature 162 and the second detent feature 164 are also contemplated.

The longitudinal position of the second detent feature 164 along the shuttle assembly 60 can correspond with a neural state of control of the articulation of the distal end portion 27 of the sheath member 15. The neural state may correspond to a neutral tension within the left and right pull wires 70, 75. Tension within the left and right pull wires 70, 75 may be neutral when there is no tension within the left and right pull wires 70, 75 or when only nominal tension from the left and right springs 90, 85 is present in the left and right pull wires 70, 75. In some embodiments, the neutral state corresponds to an axial position or range of the shuttle assembly 60 in which the shuttle assembly 60 is not engaged with the crimp tubes 106, 108, wherein engagement between the shuttle assembly 60 and one of the crimp tubes 106, 108 would otherwise increase the tension in one of the left and right pull wires 70, 75.

Indexing the neutral state with the first and the second detent feature 162, 164 can be a useful for several reasons. For example, the distal end portion 27 of the sheath member 15 will not be biased by the left and right pull wires 70, 75 to assume a deflected shape when the pull wires have neutral tension. In such case, the distal end portion 27 may assume a straight shape or offer little or no resistance to being straightened. A straight sheath member 15 is easier to withdrawal (e.g., through an introducer) when it is allowed to assume a straight shape. Also, tension remaining in either of the left and right pull wires 70, 75 can make the distal end stiff and more likely to damage tissue upon engagement.

In some embodiments, the neural state may correspond to the point at which the distal end portion 27 of the sheath member 15 is in a neutral deflection. In some embodiments, the distal end portion 27 is in the neutral deflection when it is not being deflected by either of the left and right pull wires 70, 75. In some embodiments, the distal end portion 27 is in the neutral deflection when it is in a straight configuration. As discussed previously and as shown in FIG. 1B, the distal end portion 27 of the sheath member 15 can assume several shapes by articulating in opposing directions (e.g., along a plane). Feedback indicating the neutral deflection can be useful to automatically update the user that the distal end portion 27 of the sheath member 15 is transitioning between shapes and that further rotation of the control knob 50 will begin to deflect the distal end portion 27. Without such feedback the user might not otherwise know that the sheath member 15 is being articulated in a different direction unless the user stops to view the sheath member 15 by fluoroscopy. As such, the feedback can automatically recalibrate the user's awareness of the sheath's state of deflection.

In some embodiments, the control knob 50 must be rotated through multiple full turns (each turn being 360 degrees) to articulate the distal end portion 27 of the sheath member 15 from one shape to another. Accordingly, a user may lose track of the number of times the control knob 50 has been turned, and accordingly may lose track of the corresponding shape of the distal end portion 27. Indexing the deflection of the control knob 50 (i.e. indexing each complete revolution) may still lead to confusion because each complete turn does not necessarily correspond with the neutral state. As such, the tension within the left and right pull wires 70, 75 and the deflection of the distal end portion 27 may not correspond with the angular position of the control knob 50. Instead, the tension within the left and right pull wires 70, 75 and the deflection of the distal end portion 27 can correspond with the axial position of the shuttle assembly 60 relative to the inner housing assembly 45. The first detent feature can engage the second detent feature a single time as the shuttle assembly 60 translates to the further degree in a proximal or distal direction relative to the inner housing assembly 45, the first detent feature spaced along the inner housing assembly 45 and the second detent feature spaced along the shuttle assembly 60 such that the first and second detent features engage and generate feedback when a neutral state is reached.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A deflectable introducer sheath assembly comprising:
   a tubular sheath member having a proximal end portion including a proximal end, a distal end portion terminating in a distal tip, and an internal sheath lumen extending through the proximal and distal end portions of the sheath member;
   a handle assembly coupled to the proximal end portion of the sheath member, the handle assembly including an outer housing, a control knob axially rotatable relative to the outer housing, a drive shaft within the outer housing and rotatable with the control knob relative to the outer housing, a shuttle assembly disposed about and operably engaged with the drive shaft such that rotation of the control knob and drive shaft relative to the outer housing causes axial translation of the shuttle assembly relative to the drive shaft within the outer housing, an inner housing within the outer housing enclosing the shuttle assembly, and a pulley assembly located proximal to the drive shaft and the shuttle assembly within the inner housing, the pulley assembly including:
      a pulley support member having a first side and an opposite second side;
      a first pulley shaft extending laterally from the first side of the pulley support member;
      a first pulley wheel mounted on the first pulley shaft;
      a second pulley shaft extending laterally from the second side of the pulley support member; and
      a second pulley wheel mounted on the second pulley shaft;
   a first pull wire having a distal end portion connected to the sheath member proximate the distal tip thereof, and a proximal end portion extending into the handle assembly, the proximal end portion of the first pull wire extending around and supported by the first pulley wheel and operably coupled to the shuttle assembly; and
   a second pull wire having a distal end portion connected to the sheath member proximate the distal tip thereof, and a proximal end portion extending into the handle assembly, the proximal end portion of the second pull wire extending around and supported by the second pulley wheel and operably coupled to the shuttle assembly,
   wherein axial rotation of the control knob in a first direction of rotation causes the shuttle assembly to translate proximally relative to the sheath member and thereby apply tension to the distal end portion of the first pull wire to deflect the distal end portion of the sheath member in a first direction of deflection, and wherein axial rotation of the control knob in a second direction of rotation opposite the first direction of rotation causes the shuttle assembly to translate distally relative to the sheath member and thereby apply tension to the distal end portion of the second pull wire to deflect the distal end portion of the sheath member in a second direction of deflection to provide bi-directional deflectability in the sheath member.

2. The introducer sheath assembly of claim 1, wherein the handle assembly further comprises a first spring having a first end connected to the inner housing or the outer housing and a second end connected to the first pull wire, and a second spring having a third end connected to the inner housing or the outer housing and a fourth end connected to the second pull wire, the first and second springs operable at least in part to eliminate slack in the first pull wire and the second pull wire, respectively, as the shuttle assembly translates relative to the sheath member.

3. The introducer sheath assembly of claim 1, wherein the handle assembly further includes a first stop member fixedly connected to the first pull wire and configured to engage the shuttle assembly, and a second stop member fixedly connected to the second pull wire and configured to engage the shuttle assembly.

4. The introducer sheath assembly of claim 3, wherein:
engagement between the shuttle assembly and the first stop member during proximal translation of the shuttle assembly relative to the sheath member increases tension within the first pull wire to deflect the distal end portion, and
engagement between the shuttle assembly and the second stop member during distal translation of the shuttle assembly relative to the sheath member increases tension within the second pull wire to deflect the distal end portion.

5. The introducer sheath assembly of claim 4, wherein the shuttle assembly can only engage with one of the first stop member and the second stop member a time.

6. The introducer sheath assembly of claim 3, wherein the first stop member is a first crimp tube crimped over the first wire and the second stop member is a second crimp tube crimped over the second wire.

7. The introducer sheath assembly of claim 1, wherein:
axial rotation of the control knob in the first direction of rotation causes the distal end portion to assume a first shape having a first curvature,
axial rotation of the control knob in the second direction of rotation causes the distal end portion to assume a second shape having a second curvature, and
the first shape is different than the second shape and the first curvature is different than the second curvature.

8. The introducer sheath assembly of claim 1, wherein the first direction of deflection of the distal end portion is along the same plane as the second direction of deflection of the distal end portion.

9. The introducer sheath assembly of claim 1, further comprising a feedback mechanism comprising a first detent feature on the shuttle assembly and a second detent feature on the inner handle assembly, wherein engagement between the first detent feature and the second detent feature generates feedback indicating a neutral state of the introducer sheath assembly to a user, wherein the feedback comprises at least one of sound and tactile feedback.

10. A deflectable introducer sheath assembly comprising:
a tubular sheath member having a proximal end portion including a proximal end, a distal end portion terminating in a distal tip, and an internal sheath lumen extending through the proximal and distal end portions of the sheath member;
a handle assembly coupled to the proximal end portion of the sheath member, the handle assembly comprising:
a housing;
a control knob axially rotatable relative to the housing;
a drive shaft within the housing and fixed relative to the control knob to be rotatable by the control knob;
a shuttle assembly disposed about and operably engaged with the drive shaft such that rotation of the drive shaft causes axial translation of the shuttle assembly relative to the housing; and
a pulley assembly, the pulley assembly comprising one or more pulley wheels located proximal to the drive shaft and the shuttle assembly within the inner housing;
a first pull wire having a distal end portion connected to the sheath member proximate the distal tip thereof, and a proximal end portion extending into the handle assembly, the proximal end portion of the first pull wire extending around and supported by one of the one or more pulley wheels; and
a second pull wire having a distal end portion connected to the sheath member proximate the distal tip thereof, and a proximal end portion extending into the handle assembly, the proximal end portion of the second pull wire extending around and supported by one of the one or more pulley wheels; and
a first spring having a first end connected to the housing and a second end connected to the first pull wire, and a second spring having a third end connected to the housing and a fourth end connected to the second pull wire, the first and second springs operable at least in part to eliminate slack in the first pull wire and the second pull wire, respectively, as the shuttle assembly translates relative to the sheath member, the first end located distally with respect to the second end, the third end located distally with respect to the fourth end, the first and second springs located distally of the one or more pulley wheels,
wherein rotation of the control knob in a first direction of rotation causes the shuttle assembly to translate proximally relative to the sheath member and thereby apply tension to the distal end portion of the first pull wire to deflect the distal end portion of the sheath member in a first direction of deflection, and wherein axial rotation of the control knob in a second direction of rotation opposite the first direction of rotation causes the shuttle assembly to translate distally relative to the sheath member and thereby apply tension to the distal end portion of the second pull wire to deflect the distal end portion of the sheath member in a second direction of deflection.

11. The introducer sheath assembly of claim 10, wherein the handle assembly further includes a first stop member fixedly connected to the first pull wire and configured to engage the shuttle assembly, and a second stop member fixedly connected to the second pull wire and configured to engage the shuttle assembly.

12. The introducer sheath assembly of claim 11, wherein:
engagement between the shuttle assembly and the first stop member during proximal translation of the shuttle assembly relative to the sheath member increases tension within the first pull wire to deflect the distal end portion, and engagement between the shuttle assembly and the second stop member during distal translation of the shuttle assembly relative to the sheath member increases tension within the second pull wire to deflect the distal end portion.

13. The introducer sheath assembly of claim 12, wherein the shuttle assembly can only engage with one of the first stop member and the second stop member a time.

14. The introducer sheath assembly of claim 11, wherein the first stop member is a first crimp tube crimped over the first wire and the second stop member is a second crimp tube crimped over the second wire.

15. The introducer sheath assembly of claim 10, wherein:
axial rotation of the control knob in the first direction of rotation causes the distal end portion to assume a first shape having a first curvature,
axial rotation of the control knob in the second direction of rotation causes the distal end portion to assume a second shape having a second curvature, and
the first shape is different than the second shape and the first curvature is different than the second curvature.

16. The introducer sheath assembly of claim 10, further comprising a feedback mechanism comprising a first detent feature and a second detent feature, the first detent feature connected to the shuttle assembly such that the first detent feature translates axially relative to the second detent feature when the control knob is axially rotated relative to the tubular sheath, wherein engagement between the first detent feature and the second detent feature generates feedback indicating a neutral state of the introducer sheath assembly to a user, wherein the feedback comprises at least one of sound and tactile feedback.

17. The introducer sheath assembly of claim 16, wherein the neutral state corresponds with a state of neutral tension within the first pull wire and the second pull wire.

18. A deflectable introducer sheath assembly comprising:
a tubular sheath member having a proximal end portion including a proximal end, a distal end portion terminating in a distal tip, and an internal sheath lumen extending through the proximal and distal end portions of the sheath member;
a handle assembly coupled to the proximal end portion of the sheath member, the handle assembly comprising:
a housing;
a control knob axially rotatable relative to the tubular sheath;
a drive shaft within the housing and rotatable by the control knob;
a shuttle assembly operably engaged with the drive shaft such that rotation of the drive shaft causes axial translation of the shuttle assembly relative to the tubular sheath;
a first pull wire connected to the sheath member to deflect the distal end portion of the sheath member;
a second pull wire connected to the sheath member to deflect the distal end portion of the sheath member; and
a pulley assembly distal of the drive shaft and the shuttle assembly, the pulley assembly supporting one or both of the first pull wire and the second pull wire,
wherein rotation of the control knob in a first direction of rotation causes the shuttle assembly to translate proximally relative to the sheath member and engage a first stop feature to apply tension the first pull wire, and wherein axial rotation of the control knob in a second direction of rotation opposite the first direction of rotation causes the shuttle assembly to translate distally relative to the sheath member and engage a second stop feature to apply tension the second pull wire; and
a feedback mechanism comprising a first detent feature and a second detent feature, the first detent feature connected to the shuttle assembly such that the first detent feature translates longitudinally along the handle assembly relative to the second detent feature when the control knob is axially rotated relative to the tubular sheath, the first and the second detent features configured to engage with each other to generate feedback indicating a neutral state of the introducer sheath assembly to a user, the feedback comprising at least one of a sound, a tactile event, and a change in resistance.

19. The introducer sheath assembly of claim 18, wherein one of the first or second detent features comprises a biased tab and the other of the first or second detent feature comprises one or both of a ramp and a trough with which the biased tab engages to generate the feedback.

* * * * *